United States Patent [19]

Dave et al.

[11] Patent Number: 5,352,829
[45] Date of Patent: Oct. 4, 1994

[54] SPIRO(N,N'-DINITROE-THYLENEDIAMINO)CYCLOTRIPHOSPHA-ZENES

[75] Inventors: Paritosh R. Dave, Little Falls; Farhad Forohar, Flanders, both of N.J.; Michael Chaykovsky, Columbia; Clifford D. Bedford, Silver Spring, both of Md.

[73] Assignee: The United States of America as represented by the Secretary of the Navy, Washington, D.C.

[21] Appl. No.: 42,229

[22] Filed: Apr. 2, 1993

[51] Int. Cl.$^5$ ............................................. C07F 9/547
[52] U.S. Cl. ......................................... 564/13; 149/92
[58] Field of Search ............................. 564/13; 149/92

[56] References Cited

PUBLICATIONS

Krishnamurthy et al., Inorg. Nucl. Chem. Letter, 1977, 13, 407.
Krishnamurthy et al., J. Chem. Soc. Dalton Trans., 1980, 840.
Wilson et al., Phosphorus & Sulfur, 1985, 25, 273.
Shaw, Phosphorus, Sulfur & Silicon, 1989, 45, 103.
Ruiter et al, Z. Naturforsch, 1982, 376, 1425.
Schmutzler, Inorg. Synth., 1967, 9, 75.
Vadapalli et al., Heterocycles, vol. 31, No. 12, 1990, 2231–2266.
Vadapalli et al., J. Chem. Soc. Dalton Trans. 1984, 621–625.
Chivers et al, Canadian Journal of Chemistry, vol. 50, 1972 pp. 1017–1025.
Murr et al, Journal of Molecular Structure, 117(1984), 73–85.

*Primary Examiner*—Shailendra Kumar
*Attorney, Agent, or Firm*—John D. Lewis; Roger D. Johnson

[57] ABSTRACT

Energetic nitramine containing cyclotriphosphazene which include 1,1,3,3,5,5-tris-spiro(N,N'-dinitroethylenediamino)cyclotriphosphazene, 1,1-spiro(ethylenediamino)-3,3,5,5-bis-spiro(N,N'-dinitroethylenediamino)cyclotriphosphazene, 1,1,3,3-bis-spiro(N,N'-dinitroethylenediamino)-5,5-dichlorocyclotriphosphazene, 1,1,3,3-bis-spiro(N,N'-dinitroethylenediamino)-5,5-difluorocyclotriphosphazene, 1,1-spiro(N,N'-dinitroethylenediamino)-3,3,5,5-bis-spiro(ethylenediamino)cyclotriphosphazene, 1,1-spiro(ethylenediamino)-3,3-spiro(N,N'-dinitroethylenediamino)-5,5-dichlorocyclotriphosphazene, 1,1-spiro(ethylenediamino)-3,3-spiro(N,N'-dinitroethylenediamino)-5,5-difluorocyclotriphosphazene, 1,1-spiro(N,N'-dinitroethylenediamino)-3,3,5,5-tetrachlorocyclotriphosphazene, and 1,1-spiro(N,N'-dinitroethylenediamino)-3,3,5,5-tetrafluorocyclotriphosphazene, which can be used in explosive compositions.

6 Claims, No Drawings

SPIRO(N,N'-DINITROETHYLENEDIAMINO)CYCLOTRIPHOSPHAZENES

BACKGROUND OF THE INVENTION

This invention relates to explosives and more particularly to energetic nitramine compounds for use in explosives.

Conventionally nitramine explosive compounds are carbon based. If some of the carbon can be replaced with heavier elements, higher density materials with higher detonation pressures and velocities may result. Additionally, such compounds might have reduced sensitivities. It would also be desirable to develop such compounds which also serve as energetic oxidizers.

SUMMARY OF THE INVENTION

Accordingly an object of this invention is to provide new energetic compounds for explosives.

Another object of this invention is to provide new energetic compounds with greater densities and greater detonation pressures and velocities.

A further object of this invention is to provide new energetic oxidizers for explosives.

These and other objects of this invention are accomplished by providing spiro(N,N'-dinitroethylenediamino)cyclotriphosphazenes which include 1,1,3,3,5,5-tris-spiro(N,N'-dinitroethylenediamino)cyclotriphosphazene, 1,1-spiro(ethylenediamino)-3,3,5,5-bis-spiro(N,N'-dinitroethylenediamino)cyclotriphosphazene, 1,1,3,3-bis-spiro(N,N'-dinitroethylenediamino)-5,5-dichlorocyclotriphosphazene, 1,1,3,3-bis-spiro(N,N'-dinitroethylenediamino)-5,5-difluorocyclotriphosphazene, 1,1-spiro(N,N'-dinitroethylenediamino)-3,3,5,5-bis-spiro(ethylenediamino)cyclotriphosphazene, 1,1-spiro(ethylenediamino)-3,3-spiro(N,N'-dinitroethylenediamino)-5,5-dichlorocyclotriphosphazene, 1,1-spiro(ethylenediamino)-3,3-spiro(N,N,-dinitroethylenediamino)-5,5-difluorocyclotriphosphazene, 1,1-spiro(N,N'-dinitroethylenediamino)-3,3,5,5-tetrachlorocyclotriphosphazene, and 1,1-spiro(N,N'-dinitroethylenediamino)-3,3,5,5-tetrafluorocyclotriphosphazene which are useful as energetic additives and more particularly as energetic oxidizers for explosive compositions.

DETAILED DESCRIPTION OF THE PREFERRED EMBODIMENT

CAUTION! All polynitramine compounds are considered toxic and potentially explosive and should be handled with appropriate precautions. In all nitrations with nitronium tetrafluoroborate, upon removal of acetonitrile, ice cold water must be added immediately to the residue to quench any excess $NO_2BF_4$.

The compounds of this invention are cyclotriphosphazenes having nitramine substituents on one or more phosphorous atoms. Phosphazenes are compounds whose backbones are comprised of alternating phosphorus and nitrogen atoms with two substituents on each phosphorous atom. Cyclotriphosphazenes are the cyclic six member analogs and may be represented by the following general formula

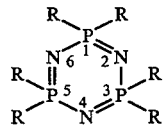

with the ring constituent numbering starting with a phosphorous atom. The corresponding chemical abstract (CAS) terminology for cyclotriphosphazenes is 1,3,5,2,4,6-triazatriphosphorines where the numbering starts with a nitrogen atom,

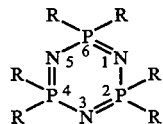

As a result, the CAS substituent numbers are 2,2,4,4,6,6-

The compounds of this invention include: 1,1,3,3,5,5-tris-spiro(N,N'-dinitroethylenediamino)cyclotriphosphazene

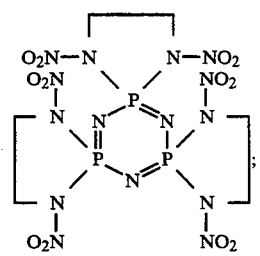

VIII 1,1-spiro(ethylenediamino)-3,3,5,5,-bis-spiro(N,N'-dinitroethylenediamino)cyclotriphosphazene,

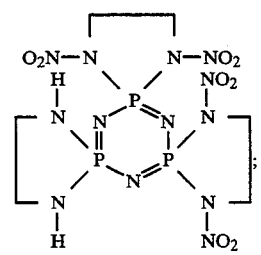

VII 1,1,3,3,-bis-spiro(N,N'-dinitroethylenediamino)-5,5-dichlorocyclotriphosphazene,

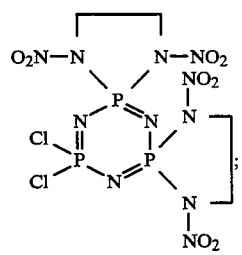

III 1,1,3,3-bis-spiro(N,N'-dinitroethylenediamino)-5,5-difluorocyclotriphosphazene,

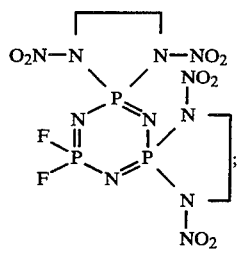

1,1-spiro(N,N'-dinitroethylenediamino)-3,3,5,5-bis-spiro(ethylenediamino)cyclotriphosphazene,

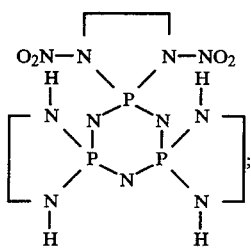

1,1-spiro(ethylenediamino)-3,3-spiro(N,N'-dinitroethylenediamino)-5,5-dichlorocyclotriphosphazene,

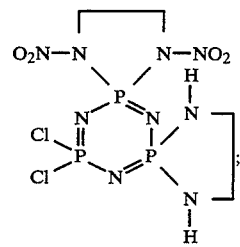

1,1-spiro(ethylenediamino)-3,3-spiro(N,N'-dinitroethylenediamino)-5,5-difluorocyclotriphosphazene,

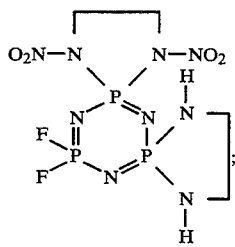

1,1-spiro(N,N'-dinitroethylenediamino)-3,3,5,5-tetrachlorocyclotriphosphazene,

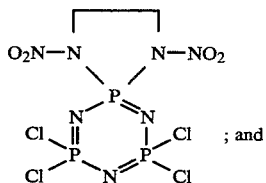

; and 1,1-spiro(N,N'-dinitroethylenediamino)-3,3,5,5-tetrafluorocyclotriphosphazene,

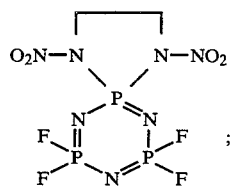

;

these compounds may be used as energetic ingredients in explosive compounds.

1,1,3,3,5,5-tris-spiro(N,N'-dinitroethylenediamino)cyclotriphosphazene, 1,1-spiro(ethylenediamino)-3,3,5,5-bis-spiro(N,N'-dinitroethylenediamino)cyclotriphosphazene, 1,1,3,3,-bis-spiro(N,N'-dinitroethylenediamino)-5,5dichlorocyclotriphosphazene, and 1,1,3,3-bis-spiro(N,N'-dinitroethylenediamino)-5,5-difluorocyclotriphosphazene are preferred because of their high energy content. Most preferred is 1,1,3,3,5,5-tris-spiro(N,N'-dinitroethylenediamino)cyclotriphosphazene which has the highest energy content and explosive power. These compounds are useful as energetic oxidizers in explosive compositions. With the exception of 1,1,3,3,5,5-tris-spiro(N,N'-dinitroethylenediamino)-cyclotriphosphazene, these compounds have the secondary utility of being precursors for 1,1,3,3,5,5-tris-spiro(N,N'-dinitroethylenediamino)cyclotriphosphazene.

The most preferred compound of this invention, 1,1,3,3,5,5-tris-spiro(N,N'-dinitroethylenediamino)cyclotriphosphazene, can be prepared by two methods. The first method can be summarized as follows:

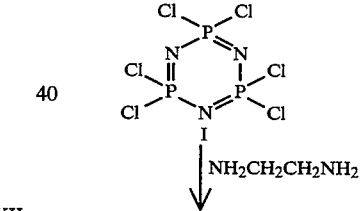

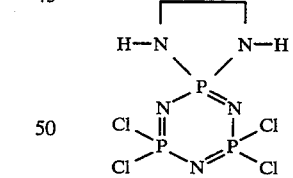

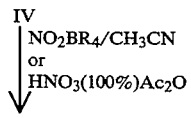

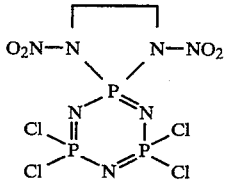

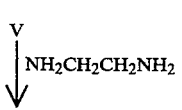

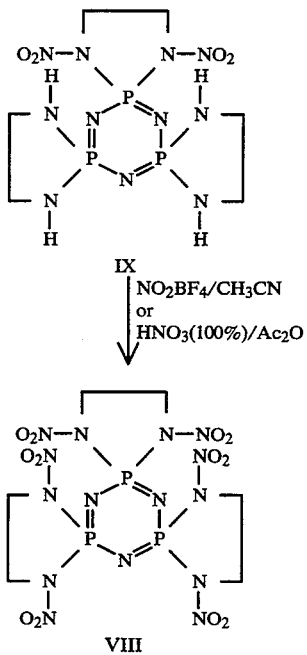

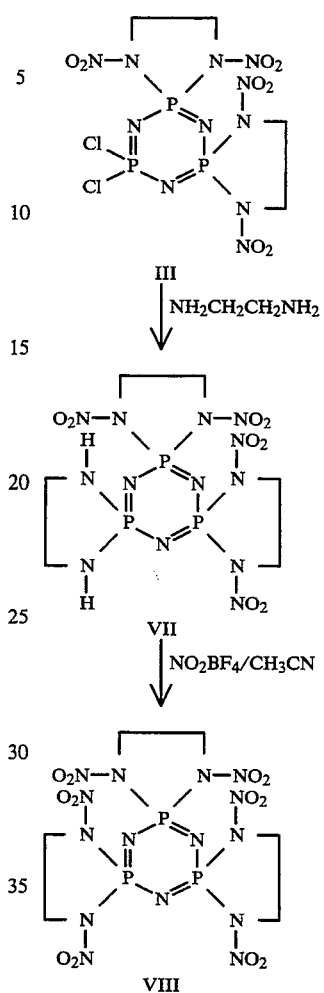

The 1,1-spiro(ethylenediamino)-3,3,5,5-tetrachlorocyclotriphosphazene, IV, starting materials is prepared by treating hexachlorocyclotriphosphazene, I, with ethylenediamine by the method of Krishnamurthy et al. *Inorg. Nucl. Chem. Lett.*, 1977, 13, 407; b) ibid. *J. Chem. Soc. Dalton Trans.*, 1980, 840; hereby incorporated by reference in their entirety. The 1,1-spiro(ethylenediamino)-3,3,5,5-tetrachlorocyclotriphosphazene, IV, is then nitrated by using either nitronium tetrafluoroborate in acetonitrile or with an acetic anhydride/100% nitric acid mixture to give 1,1-spiro(N,N'-dinitroethylenediamino)-3,3,5,5-tetrachlorocyclotriphosphazene, V, (see example 2 for reaction conditions). The 1,1-spiro(N,N'-dinitroethylenediamino)-3,3,5,5-tetrachlorocyclotriphosphazene, V, was then treated with excess ethylenediamine under reflux to give 1,1-spiro(N,N'-dinitroethylenediamino)-3,3,5,5-bis-spiro(ethylenediamino) cyclotriphosphazene, IX (see example 6 for reaction conditions). 1,1,3,3,5,5,-tris-spiro(N,N'-dinitroethylenediamino)cyclotriphosphazene, VIII, is prepared by nitrating 1,1-spiro(N,N'-dinitroethylenediamino)-3,3,5,5-bis-spiro(ethylenediamino)cyclotriphosphazene, IX, by using either nitronium tetrafluoroborate in acetonitrile or with an acetic anhydride/100% nitric acid mixture (reaction conditions for both of these nitration procedures are illustrated in method B of example 5). As shown in example 5, method B, the yield using acetic anhydride/100% nitric acid was 90% as compared to 66% using nitronium tetrafluoroborate in acetonitrile.

The second method of preparing 1,1,3,3,5,5-tris-spiro(N,N'-dinitroethylenediamino)cyclotriphosphazene, can be summarized as follows:

1,1-spiro(ethylenediamino)-3,3,5,5-bis-spiro(N,N'-dinitroethylenediamino)cyclotriphosphazene, VII, is prepared by reacting 1,1,3,3-bis-spiro(N,N'-dinitroethylenediamino)-5,5-dichlorocyclotriphosphazene, III, with ethylenediamine. Although the reaction is slow, a good yield is obtained by refluxing the reaction mixture for about 24 hours (see example 4 for reaction conditions). The 1,1-spiro(ethylenediamino)-3,3,5,5-bis-spiro(N,N'-dinitroethylenediamino)cyclotriphosphazene, VII, is then nitrated by using either nitronium tetrafluoroborate in acetonitrile on with an acetic anhydride/100% nitric acid mixture to give 1,1,3,3,5,5-tris-spiro(N,N'-dinitroethylenediamino)cyclotriphosphazene, VIII, (see method A of Example 5 for reaction conditions). As shown in example 5, method A, the yield using acetic anhydride/100% nitric acid was 93% as compared to 63% using nitronium tetrafluoroborate in acetonitrile.

1,1,3,3-Bis-spiro(N,N'-dinitroethylenediamino)-5,5-dichlorocyclotriphosphazene, III, which is used in second method above, can be produced in two ways. The first way of producing 1,1,3,3-bis-spiro(N,N'-dinitroethylenediamino)-5,5-dichlorocyclotriphosphazene, III, can be summarized as follows:

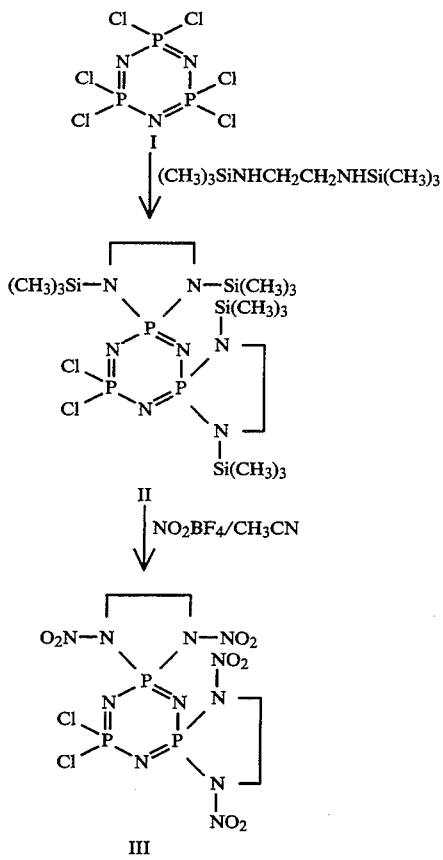

1,1,3,3-Bis-spiro-(N,N'-bistrimethylsilyl-ethylenediamino)-5,5-dichlorocyclotriphosphazene, II, can be produced by treating hexachlorocyclotriphosphazene, I, with an excess of N,N'-bis(trimethylsilyl)ethylenediamine in refluxing tetrahydrofuran (THF) (see example 1 for reaction conditions). After aqueous workup, the product mixture contains principally 1,1,3,3-bis-spiro-(N,N'-bistrimethylsilyl-ethylenediamino)-5,5-dichlorocyclotriphosphazene, II, which can be used without further purification. Nitration of 1,1,3,3-bis-spiro-(N,N'-bistrimethylsilyl-ethylenediamino)-5,5-dichlorocyclotriphosphazene, II, with nitronium tetraborotrate in acetonitrile gives 1,1,3,3-bis-spiro(N,N'-dinitroethylenediamino)-5,5-dichlorocyclotriphosphazene, III, (see example 1 for reaction conditions).

The second way of producing 1,1,3,3-bis-spiro(N,N'-dinitroethylenediamino)-5,5-dichlorocyclotriphosphazene, III, can be summarized as follow:

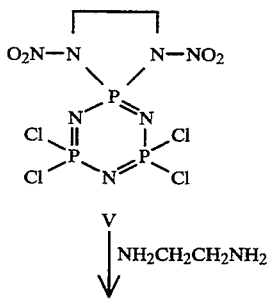

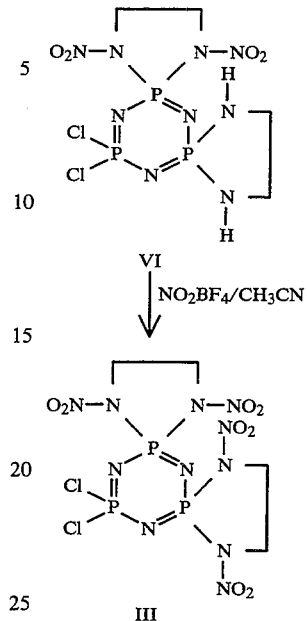

The 1,1-spiro(N,N'-dinitroethylenediamino)-3,3,5,5-tetrachlorocyclotriphosphazene, V, is produced according to the method disclosed above. Brief treatment of the 1,1-spiro(N,N'-dinitroethylenediamino)-3,3,5,5-tetrachlorocyclotriphosphazene, V, with an excess of ethylenediamine in methylene chloride produces 1,1-spiro(ethylenediamino)-3,3-spiro(N,N'-dinitroethylenediamino)-5,5-dichlorocyclotriphosphazene, VI, (see example 3 for reaction conditions). The 1,1-spiro(ethylenediamino)-3,3-spiro(N, N'-dinitroethylenediamino)-5,5-dichlorocyclotriphosphazene, VI, is then nitrated with nitronium tetrafluoroborate in acetonitrile to give 1,1,3,3-bis-spiro(N, N'-dinitroethylenediamino)-5,5dichlorocyclotriphosphazene, III (see example 1 for reaction conditions).

The process for preparing 1,1,3,3-bis-spiro(N,N'-dinitroethylenediamino)-5,5-difluorocyclotriphosphazene, XIII, can be summarized as follows:

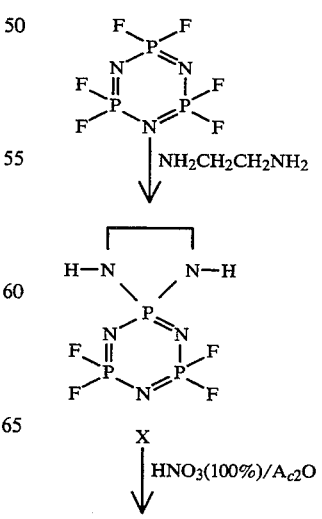

-continued

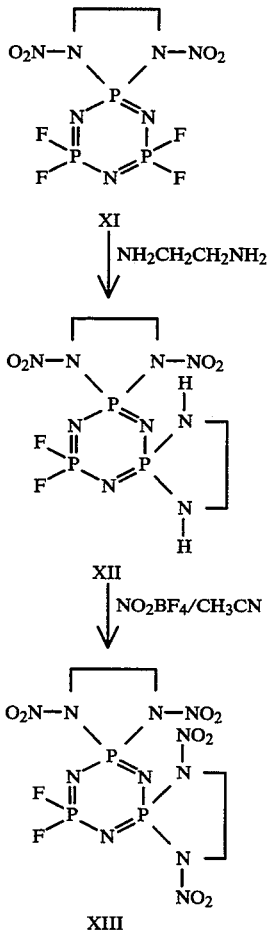

Hexafluorocyclotriphosphazene is treated with ethylenediamine in methylene chloride to give 1,1-spiro(ethylenediamino)-3,3,5,5-tetrafluorocyclotriphosphazene, X, (see example 7 for reaction conditions). The 1,1-spiro(ethylenediamino)-3,3,5,5-tetrafluorocyclotriphosphazene, X, can be nitrated by using an acetic anhydride/100% nitric acid mixture to give 1, 1-spiro(N,N'-dinitroethylenediamino)-3,3,5,5-tetrafluorocyclotriphosphazene, XI, (see example 8 for reaction conditions). The 1,1-spiro(N,N'-dinitroethylenediamino)-3,3,5,5-tetrafluorocyclotriphosphazene, XI, is treated with ethylenediamine to give 1,1-spiro(ethylenediamino)-3,3-spiro(N,N'-dinitroethylenediamino)5,5-difluorocyclotriphosphazene, XII, (see example 9 for the reaction conditions). Finally, the 1,1-spiro(ethylenediamino)3,3-spiro(N,N'-dinitroethylenediamino)-5, 5-difluorocyclotriphosphazene, XII, is nitrated using nitronium tetrafluoroborate in acetonitrile to give 1,1,3,3-bis-spiro (N,N'-dinitroethylenediamino)-5,5-difluorocyclotriphosphazene, XIII (see example 10 for the reaction conditions).

1,1,3,3-bis-spiro(N,N'-dinitroethylenediamino)-5,5difluorocyclotriphosphazene, XIII, may be substituted for 1,1,3,3-bis-spiro(N,N'-dinitroethylenediamino)-5,5-dichlorocyclotriphosphazene, III, in the processes discussed above.

The general nature of the invention having been set forth, the following examples are presented as specific illustrations thereof. It will be understood that the invention is not limited to these specific examples but is susceptible to various modifications that will be recognized by one of ordinary skill in the art. CAUTION! All polynitramine compounds are considered toxic and potentially explosive and should be handled with appropriate precautions. In all nitrations with nitronium tetrafluoroborate, upon removal of acetonitrile, ice cold water must be added immediately to the residue to quench any excess $NO_2BF_4$.

Melting points are uncorrected. NMR spectra were recorded on a Bruker NR 300 spectrometer. Chemical shifts are reported in ppm downfield from internal tetramethylsilane except for $^{31}p$ NMR spectra, which are referenced to phosphoric acid. Tetrahydrofuran (THF) was dried by distilling from benzophenone ketyl. Hexachlorocyclotriphosphazene was obtained from Aldrich Chemical Co. and nitronium tetrafluoroborate from Ozark-Mahoning, Inc. All spirocyclotriphosphazenes incorporating both NH and P-Cl linkages were found to be moisture sensitive and unstable in solution. These materials were used immediately without further purification in subsequent reaction steps. Elemental analyses were performed by Galbraith Laboratories, Inc., Knoxville, Tenn.

EXAMPLE 1

1,1,3,3-Bis-spiro(N,N'-dinitroethylenediamino)-5,5-dichlorocyclotriphosphazene, III A solution of hexachlorocyclotriphosphazene, I (20.0 g, 57.3 mmol) in dry THF (180 mL) was added dropwise to a refluxing solution of N,N'-bis(trimethylsilyl)ethylenediamine (60.0 g, 294 mmol) in THF (500 mL) under an inert atmosphere over 4 hours. The mixture was then stirred at reflux overnight. The resulting mixture was cooled to room temperature and concentrated under reduced pressure. Upon removal from the rotary evaporator, ice cold water (300 mL) was added immediately and the resulting cloudy solution extracted with methylene chloride (3×200 mL). The organic extracts were combined and dried over $MgSO_4$. The solution was then filtered and concentrated in vacuo to yield a viscous material.

The material obtained above was stirred in dry acetonitrile (500 mL) for 10 minutes. The suspension was then cooled in an ice bath (5°–10° C.) and nitronium tetrafluoroborate (31.3 g, 236 mmol) was added over a 10 minute period. The solution was stirred for another 2 hours at 5°–10 ° C., and then concentrated under reduced pressure. To the residue ice cold water (800 mL) was immediately added and the mixture stirred for 30 minutes whereupon the product separated as a white solid and was collected by filtration. Recrystallization from aqueous acetone yielded 1,1,3,3,-bis-spiro(N,N'-dinitroethylenediamino)-5,5-dichlorocyclotriphosphazene, as a colorless solid (21.2 g, 73% from hexachlorocyclotriphosphazene), mp 242°–244° C.

Alternatively, $NO_2BF_4$ (1.5 g, 11.3 mmol) was added to an ice cooled solution of 1,1-spiro(ethylenediamino)-3,3-spiro(N,N'-dinitroethylenediamino)-5,5-dichlorocyclotriphosphazene (1.6 g, 3.8 mmol) in acetonitrile under dry atmosphere and the resulting solution was stirred at 0° C. for an hour. The cooling bath was removed and stirring was continued overnight. The reaction mixture was then concentrated under reduced pressure and to the residue was immediately added ice cold water and methylene chloride. The organic phase was separated, washed successively with saturated $NaHCO_3$ solution, and brine, then dried ($Na_2SO_4$), filtered and concentrated. The residue was chromatographed on silica gel to give 1,1,3,3-bis-spiro(N,N'-dinitroethylenediamino)-5,5-dichlorocyclotriphosphazene (1.0 g, 2.0 mmol, 52%).

(CAUTION: 1,1,3,3-bis-spiro(N,N'-dinitroethylenediamino)-5,5-dichlorocyclotriphosphazene exhibits explosive behavior on heating).

IR (KBr), 1570 (N-NO$_2$), 1275 (N-NO$_2$), 1195 cm$^{-1}$; $^1$H NMR (acetone-d$_6$) δ4.25–4.50 (m); $^{13}$C NMR (acetone d$_6$) δ43.0 (br.): $^{31}$P NMR (acetone-d$_6$) δ0.0 (d) δ38.0 (t,J$_{p-p}$=68.8 Hz). Anal. Calcd for C$_4$H$_8$$^{35}$Cl$_2$N$_{11}$O$_8$P$_3$: (M+H)$^+$, 500.9147 Found (M+H)$^+$, 500.9142.

EXAMPLE 2

1,1-Spiro(N,N'-dinitroethylenediamino)-3,3,5,5-tetrachlorocyclotriphosphazene, V To a cooled solution (5°–7° C.) of 1,1-spiro(ethylenediamino)-3,3,5,5-tetrachlorocyclotriphosphazene (1.6 g, 5 mmol) in acetonitrile (50 mL) was added nitronium tetrafluoroborate (1.5 g, 11.3 mmol) in one portion. The resulting suspension was stirred at 5°–7° C. for one hour and then stirred overnight at room temperature. The reaction mixture was then concentrated under reduced pressure. The residue was taken up in methylene chloride (50 mL) and washed successively with water (50 mL), saturated NaHCO$_3$ solution (50 mL) and brine (50 mL). The organic phase was dried over MgSO$_4$, filtered and the filtrate was concentrated in vacuo to give a pale yellow solid. Recrystallization from acetone-hexanes afforded pure 1,1-spiro(N,N'-dinitroethylenediamino)-3,3,5,5-tetrachlorocyclotriphosphazene as a colorless microcrystalline solid (1.1 g, 2.6 mmol, 52%), mp 225°–227° C.

Alternatively, 100% nitric acid (3.0 g, 47.6 mmol) was added dropwise with stirring to acetic anhyride (7.39 g, 72.4 mmol) cooled to −5° C. (salt-ice). The solution was then warmed to 20° C. over 1 hour, cooled again to −5° C., and to this was added 1,1-spiro(ethylenediamino)-3,3,5,5-tetrachlorocyclotriphosphazene, IV (1.0 g, 3.0 mmol) all at once. After stirring at −5° C. for 1.5 hours, the mixture was poured onto a mixture of ice and water (50mL), and the precipitated white solid was filtered, washed with cold water and dried to give 1,1-spiro(N,N'-dinitroethylenediamino)3,3,5,5-tetrachlorocyclotriphosphazene (1.13 g, 89%): mp 223°–226° C. Recrystallization from benzene-hexane gave colorless prisms: mp 225°–227° C. IR (KBr) 1575 (N-NO$_2$), 1275 (N-NO$_2$) 1210 cm$^{-1}$ (PNP); $^1$H NMR (CDCl$_3$) δ4.10 (d, J$_{P-H}$=6.6 Hz); $^{13}$C NMR (CDCl$_3$) δ 41.0 (d, J$_{C-P}$=10.13 Hz); $^{31}$P NMR (CDCl$_3$) δ−7.2 (t), δ28.6 (d, J$_{P-P}$=59.1 Hz). HRMS EI (M=H)$^+$Calcd. 422.8291; Found 422.8301. Anal. Calcd. for C$_2$H$_4$Cl$_4$N$_7$O$_4$P$_3$: C, 5.65; H, 0.95; Cl, 33.38; N, 23.08; P, 21.87. Found: C, 6.14; H, 0.95; Cl, 33.68; N, 22.47; P, 21.99.

EXAMPLE 3

1,1-Spiro(ethylenediamino)-3,3-spiro(N,N'-dinitroethylenediamino)-5,5-dichlorocyclotriphosphazene, VI Ethylenediamine (1.0 g, 12.5 mmol) was slowly added to a stirred solution of 1,1-spiro(N,N'-dinitroethylenediamino)-3,3,5,5-tetrachlorocyclotriphosphazene (0.05 g, 0.11 mmol) in methylene chloride (15 mL) at 25° C. The mixture was stirred at 25° C. for one hour. A suspension was obtained and was extracted with water (60 mL). The organic layer was kept over CaCl$_2$ for one hour, filtered, and concentrated by rotary evaporator to yield 1,1-spiro(ethylenediamino)-3,3-spiro(N,N'-dinitroethylenediamino)-5,5-dichlorocyclo triphosphazene (0.04 g, 81%). IR (KBr) 3400 (NH), 2890 (NH), 1550 (N-NO$_2$), 1270 (N-NO$_2$), 1230 (PNP) cm$^{-1}$; $^1$H NMR (acetone-d$_6$) δ2.81 (d), 3.45 (m), δ4.10 (d, J$_{C-P}$=10.5 Hz); $^{13}$C NMR (CDCl$_3$) δ41.3 (d, J$_{C-P}$=9.0 Hz), 42.1 (d, J$_{C-P}$=10.5 Hz).

EXAMPLE 4

1,1-Spiro(ethylenediamino)-3,3,5,5-bis-spiro(N,N'-dinitroethylenediamino)cyclotriphosphazene, VII To a refluxing solution of ethylenediamine (54 g, 900 mmol) in methylene chloride (150 mL) under inert atmosphere was added dropwise a solution of 1,1,3,3-bis-spiro(N,N'-dinitroethylenediamino)-5,5-dichlorocyclotriphosphazene (12 g, 24 mmol) in methylene chloride (150 mL) over two hours. Additional methylene chloride (100 mL) was then added and the resulting suspension was heated at reflux for a further 24 hours. The solvent was removed by rotary evaporation and the resulting residue was suspended in water. Product 1,1-spiro(ethylenediamino)-3,3, 5,5-bis-spiro(N,N'-dinitroethylenediamino)cyclotriphosphazene was collected by filtration (9.0 g, 20 mml, 84%), mp 145°–149° C.: IR (KBr) 3450 (NH), 2880 (NH), 1550 (N-NO$_2$), 1275 (N-NO$_2$), 1230 cm$^{-1}$ (PNP); $^1$H NMR (DMSO-d$_6$) δ3.15 (d, 4H, J$_{H-P}$=12.6 Hz), δ4.1 (d of m, 8H), δ4.4 (d, 2H, J$_{H-P}$=14.6 Hz); $^{31}$P (DMSO-d$_6$); δ5.4 (d, J$_{P-P}$=56.6 Hz), δ35.0 (t, J$_{P-P}$=56.6 Hz). HRMS m/e Calcd. for (C$_6$H$_{15}$N$_{13}$O$_8$P$_3$)+490.0379. Found 490.0383.

EXAMPLE 5

1,1,3,3,5,5,-Tris-spiro(N,N'-dinitroethyenediamino)cyclotriphosphazene, VIII.

Method A. A suspension of 1,1-spiro(ethylenediamino)3,3,5,5-bis-spiro(N,N -dinitroethylenediamino) cyclotriphosphazene, (28.7 g, 58.6 mmol) in CH$_3$CN (700 mL) was stirred at ice bath temperature and NO$_2$BF$_4$ (16.4 g, 123.5 mmol) was added to it over ten minutes. The resulting clear colorless solution was stirred at 0°–5° C. for 2 hours. The solvent was then removed under vacuum and the resulting yellow solid was immediately added to 500 mL of ice cold water. Continued stirring gave 1,1,3,3,5,5,-tris-spiro(N,N'-dinitroethyenediamino)cyclotriphosphazene as a faint-yellow solid (21.3 g, 36.9 mmol, 63%). This solid was washed with methanol (15 mL) and recrystalled from 5% aqueous acetone to give pure 1,1,3,3,5,5,-tris-spiro(N,N'-dinitroethyenediamino) cyclotriphosphazene, m.p. 203°–205° C. (dec.). CAUTION; Compound 1,1-spiro(ethylenediamino)-3,3,5,5-bis-spiro(N,N'-dinitroethylenediamino)cyclotriphosphazene exhibits explosive behavior on heating or when subjected to shock.

Alternatively, compound 1,1,3,3,5,5,-tris-spiro(N,N'-dinitroethyenediamino)cyclotriphosphazene was prepared by treating 1,1-spiro(ethylenediamino)-3,3,5,5-bis-spiro(N,N'-dinitroethylenediamino)cyclotriphosphazene with acetylnitrate. To 12 mL of 100% acid cooled to −5° C. was added dropwise with stirring 78 mL of acetic anhydride. The mixture was warmed to room temperature and stirred for an additional hour. It was then cooled to −5° C. whence compound 1,1-spiro(ethylenediamino)3,3,5,5-bis-spiro(N,N'-dinitroethylenediamino) cyclotriphosphazene (12.7 g 25.9 mmol) was added at once. The resulting suspension was stirred at −5° C. for one hour and then at room temperature for 3 hours more. The crude product was poured over ice (300 g), and the precipitated white product, 1,1,3,3,5,5,-tris-spiro(N,N'-dinitroethyenediamino)cyclotriphosphazene, (14.0 g 24.1 mmol, 93%) was collected by filtration.

Method B. A stirred suspension of 1,1-spiro(N,N'-dinitroethylenediamino)-3,3, 5,5-bis-spiro(ethylenediamino)cyclotriphosphazene (399 mg, 1.0 mmol) in CH$_3$CN (30 mL) was cooled to 0° C. and then NO$_2$BF$_4$ (671 mg of 84%, 5.0 mmol) was added all at once. The resulting solution was stirred at 0° C. for 4 hours and then evaporated under vacuum to give a pale yellow oil. Addition of water (25mL) precipitated a white solid which was filtered, washed with methanol, and dried to yield 1,1,3,3,5,5,-tris-spiro(N,N'-dinitroethyenediamino)cyclotriphosphazene, VIII (380 mg, 66%): mp 203°-205° C. (dec).

Compound 1,1,3,3,5,5,-tris-spiro(N,N'-dinitroethyenediamino)cyclotriphosphazene VIII was also prepared by treating 1,1-spiro(N,N'-dinitroethylenediamino)3,3,5,5,bis-spiro(ethylenediamino)cyclotriphosphazene with acetylnitrate. Nitric acid (3.0 g, 47.6 mmol of 100%) was added dropwise with stirring to acetic anhydride (7.39 g, 72.4 mmol) cooled to −5° C. (salt-ice). The solution was then warmed to 20° C. over 1 hour, cooled again to −5° C. and to this was added 1,1-spiro(N,N'-dinitroethylenediamino)-3,3,5,5-bis-spiro(ethylenediamino)cyclotriphosphazene, (1.197 g, 3.0 mmol) all at once. After stirring at −5° C. for 2 hours the solution was poured onto a mixture of ice and water (150mL) and the precipitated white solid filtered, washed with water (50mL), then with methanol (25mL) and dried to give 1,1,3,3,5,5,-tris-spiro(N,N'-dinitroethyenediamino)cyclotriphosphazene (1.595 g, 90%): mp 203°-205° C. (dec). Recrystallization from acetone-methanol gave colorless prisms: mp 205° C. (violent dec). IR (KBr) 1580 (N-NO$_2$), 1285 (N-NO$_2$), 1200 cm$^{-1}$(PNP): $^1$H NMR (acetone-d$_6$) δ4.3 (m); $^{13}$C NMR (acetone-d$_6$) δ42.5 (d, J$_{C-P}$=9.8 Hz); $^{31}$P NMR (acetone-d$_6$) δ5.7 (s). HRMS CI (NH$_3$) m/e Calcd. 597.0346. Found: 597.0352. Anal. Calcd for C$_6$H$_{12}$N$_{15}$O$_{12}$P$_3$: C, 12.44; H, 2.09; N, 36.28; P, 16.04. Found: C, 12.42; H, 2.02; N, 35.87; P, 16.09.

EXAMPLE 6

1,1-Spiro(N,N'-dinitroethylenediamino)-3,3,5,5-bis-spiro(ethylenediamino)cyclotriphosphazene, IX.

A solution of ethylenediamine (3.60 g, 60 mmol) in CH$_2$Cl$_2$ (100 mL) was added dropwise over 1 hour to a stirred, refluxing solution of 1,1-spiro(N,N'-dinitroethylenediamino)-3,3,5,5tetrachlorocyclotriphosphazene (4.25 g, 10 mmol) in CH$_2$Cl$_2$ (50 mL). Refluxing was continued for an additional 24 hours, during which time a white solid precipitated. The mixture was cooled and the solid filtered, suspended in water (130 mL), and the pH brought to 9 by the addition of NH$_4$OH. After stirring for 30 minutes the solid was filtered, washed with water (50 mL), then acetone (20 mL), and dried to give 1,1-spiro(N,N'-dinitroethylenediamino)-3,3, 5,5-bis-spiro(ethylenediamino)cyclotriphosphazene(3.67 g, 92%): mp 278°-280° C. (dec). The analytical sample, recrystallized from DMF, had mp 290° C. (dec). IR (KBr) 1540 (N-NO$_2$) 1280 and 1250 cm$^{-1}$ (N-NO$_2$ and/or PNP); $^1$H NMR (DMSO-d$_6$) δ3.97(d, 4, 2CH$_2$s), δ3.77 (m, 4, NHs), δ3.00 (m, 8, 4CH$_2$). Anal. Calcd for C$_6$H$_{16}$N$_{11}$O$_4$P$_3$: C, 18.05; H, 4.04; N, 38.60; P, 23.28. Found: C, 18.42; H, 4.31; N, 38.11; P, 23.03.

EXAMPLE 7

1,1-Spiro(ethylenediamino)-3,3,5,5,-tetrafluorocyclotriphosphazene, X.

To a solution of hexafluorocyclotriphosphazene (31 g) was added a solution of ethylenediamine (21 g) in methylene chloride (25 mL) in 1 hour. The reaction was exothermic and maintained at 25° C. After stirring for a further 24 hours at room temperature the mixture was extracted with water. The organic was dried (MgSO$_4$), filtered, and the filtrate was concentrated under reduced pressure to give 1,1-Spiro(ethylenediamino)-3,3,5,5-tetrafluorocyclotriphosphazene, as a white solid (24 g, 71%). mp 125° C.; $^1$H NMR (CDCl$_3$) δ2.7 (d, N-H,J=10.8 Hz), 3.45 (d, CH$_2$, J=12.6 Hz); $^{13}$C NMR (CDCl$_3$) δ42.4 (d, J=11.32 Hz); $^{31}$P NMR (CDCl$_3$) δ11.6 (m, t, J$_{P-F}$=882 Hz), δ31.7 (m, t, J$_{P-P}$=95.1 Hz)

EXAMPLE 8

1,1-Spiro(N,N'-Dinitroethylenediamino)-3,3,5,5-tetrafluorocyclotriphosphazene, XI.

To ice cooled acetic anhydride (86 mL) was added very carefully 100% nitric acid (23 mL) dropwise over two hours. The solution was then stirred for one hour at 24° C., again cooled to 0° C. and 1,1-spiro(ethylenediamino)-3,3,5,5-tetrafluorocyclotriphosphazene (9 g) was added to it in one portion. The resulting mixture was stirred at 0° C. for two hours and then poured over ice and the precipitated product, 1,1-spiro(N,N'-dinitroethylenediamino)-3,3,5,5-tetrafluorocyclotriphosphazene was collected by filtration (9.1 g, 76%).

mp 117° C.; $^1$H NMR (CDCl$_3$) δ4.17 (d, J=6.7 Hz); $^{13}$C NMR (CDCl$_3$) 4.15 (d, J=9.7 Hz); $^{31}$P NMR (CDCl$_3$) δ11.7 (m,t J$_{P-F}$=940 Hz), δ4.2 (m).

EXAMPLE 9

1,1-Spiro(ethylenediamino)-3,3-spiro(N,N'-dinitroethylenediamino)-5,5-difluorocyclotriphosphazene, XII.

To a solution of 1,1,spiro(N,N'-dinitroethylenediamino)-3,3,5,5-tetrafluorocyclotriphosphazene (0.5 g) in CH$_2$Cl$_2$ (90 ml) was added diethylenediamine (1.0 g, 16.6 mmol). The solution was stirred at 25° C. for two hours and then filtered, and the filtrate was concentrated by rotary evaporation to give 1,1-spiro(ethylenediamino)-3,3-spiro(N,N'-dinitroethylenediamino)-5,5-difluorocyclotriphosphazene as an oil (0.6 g). This compound exhibited instability in solution and so was used without further purification

EXAMPLE 10

1,1,3,3-Bis-spiro(N,N'-dinitroethylenediamino)-5,5-difluorocyclotriphosphazene, XIII.

To a solution of 1,1-spiro(ethylenediamino)-3,3-spiro(N,N'-dinitroethylenediamino)-5,5-difluorocyclotriphosphazene (0.19 g) in CH$_3$CN 35 ml) was added NO$_2$BF$_4$ (0.6 g). The mixture was stirred at 25° C. for 45 minutes and then concentrated by rotary evaporation to give a thick yellow oil which was partitioned between water and CHCl$_3$. The organic layer was separated, dried over MgSO$_4$ and concentrated by rotary evaporation to a yellow oil. Diethyl ether was added to the oil; a yellow precipitate began to form in about two minutes. The precipitate was collected by filtration and dried to a constant weight (30 mg, 12% yield). mp 209°-211° C.; $^1$H NMR (acetone, d6) δ4.24-4.46 (d,m, J=46.6 Hz); $^{13}$C NMR (acetone, d6) δ43.1; $^{31}$P NMR (acetone, d6) δ16.2 (d,d,t, J$_{P-F}$=905 Mz) δ5.15–6.74 (d,m, J=64.8 Hz).

Numerous other modifications and variations of the present invention are possible in light of the foregoing teachings. It is therefore to be understood that within the scope of the appended claims the invention may be practiced otherwise than as specifically described.

What is claimed is:

1. A compound that is 1,1,3,3,5,5-tris-spiro(N,N'-dinitroethylenediamino)cyclotriphosphazene, 1,1,-spiro(ethylenediamino)-3,3,5,5-bis-spiro(N,N'-dinitroethylenediamino)cyclotriphosphazene, 1,1,3,3-bis-spiro(N,N'-dinitroethylenediamino)-5,5-dichlorocyclotriphosphazene, 1,1,3,3-bis-spiro(N,N'-dinitroethylenediamino)-5,5-difluorocyclotriphosphazene, 1,1-spiro(N,N'-dinitroethylenediamino)-3,3,5,5-bis-spiro(ethylenediamino)cyclotriphosphazene, 1,1-spiro(ethylenediamino)-3,3-spiro(N,N'-dinitroethylenediamino)-5,5-dichlorocyclotriphosphazene, 1,1-spiro(ethylenediamino)-3,3-spiro(N,N'-dinitroethylenediamino)-5,5-difluorocyclotriphosphazene, 1,1-spiro(N,N'-dinitroethylenediamino)-3,3,5,5-tetrachlorocyclotriphosphazene, or 1,1-spiro(N,N'-dinitroethylenediamino)-3,3,5,5-tetrafluorocyclotriphosphazene.

2. The compound of claim 1 that is 1,1,3,3,5,5-tris-spiro(N,N'-dinitroethylenediamino)cyclotriphosphazene, 1,1-spiro(ethylenediamino)-3,3,5,5-bis-spiro(N,N'-dinitroethylenediamino)cyclotriphosphazene, 1,1,3,3-bis-spiro(N,N'-dinitroethylenediamino)-5,5-dichlorocyclotriphosphazene, or 1,1,3,3-bis-spiro(N,N'-dinitroethylenediamino)-5,5-difluorocyclotriphosphazene.

3. The compound of claim 2 that is 1,1,3,3,5,5-tris-spiro(N,N'-dinitroethylenediamino)cyclotriphosphazene.

4. The compound of claim 2 that is 1,1-spiro(ethylenediamino)-3,3,5,5-bis-spiro(N,N'-dinitroethylenediamino)cyclotriphosphazene.

5. The compound of claim 2 that is 1,1,3,3-bis-spiro(N,N'-dinitroethylenediamino)-5,5-dichlorocyclotriphosphazene.

6. The compound of claim 2 that is 1,1,3,3-bis-spiro(N,N'-dinitroethylenediamino)-5,5-difluorocyclotriphosphazene.

* * * * *